United States Patent
Mellersh et al.

(10) Patent No.: US 9,752,195 B2
(45) Date of Patent: Sep. 5, 2017

(54) TTC8 AS PROGNOSTIC GENE FOR PROGRESSIVE RETINAL ATROPHY IN DOGS

(71) Applicant: Animal Health Trust, Kentford, Newmarket, Suffolk (GB)

(72) Inventors: Cathryn Suzanne Mellersh, Newmarket (GB); Louise Mary Downs, Newmarket (GB)

(73) Assignee: Animal Health Trust, Newmarket (GB)

( * ) Notice: Subject to any disclaimer, the term of this patent is extended or adjusted under 35 U.S.C. 154(b) by 160 days.

(21) Appl. No.: 14/404,291

(22) PCT Filed: May 24, 2013

(86) PCT No.: PCT/GB2013/051365
§ 371 (c)(1),
(2) Date: Nov. 26, 2014

(87) PCT Pub. No.: WO2013/179001
PCT Pub. Date: Dec. 5, 2013

(65) Prior Publication Data
US 2015/0148406 A1    May 28, 2015

(30) Foreign Application Priority Data

May 28, 2012 (GB) .................................. 1209420.7

(51) Int. Cl.
*C07H 21/04* (2006.01)
*C12Q 1/68* (2006.01)
(52) U.S. Cl.
CPC ...... *C12Q 1/6883* (2013.01); *C12Q 2600/118* (2013.01); *C12Q 2600/156* (2013.01)
(58) Field of Classification Search
None
See application file for complete search history.

(56) References Cited

U.S. PATENT DOCUMENTS 5,686,598 A    11/1997    North et al.

FOREIGN PATENT DOCUMENTS

| WO | WO 01/38578 A1 | 5/2001 |
| WO | WO 2007/122279 A2 | 11/2007 |
| WO | WO 2010/092417 A1 | 8/2010 |

OTHER PUBLICATIONS

Genbank Accession No. XM_003639207, Dec. 2, 2011, from IDS.*
Yi et al. (Genbank, CF411203, Sep. 2, 2003).*
Edelstein et al. Gene therapy clinical trials worldwide 1989-2004—an overview. Journal of Gene Medicine, vol. 6, pp. 597-602, 2004.*
Verma and Weitzman, Gene Therapy: Twenty-first century medicine. Annual Review of Biochemistry, vol. 74, pp. 711-738, 2005.*
Domvri et al (Gene therapy in liver diseases: State-of-the-art and future perspectives. Current Gene Therapy, vol. 12, pp. 463-483, Dec. 2012).*
Luo et al (Synthetic DNA delivery systems. Nature Biotechnology, vol. 18, pp. 33-37, 2000).*
Palù et al (In pursuit of new developments for gene therapy of human diseases. Journal of Biotechnology. vol. 68, pp. 1-13, 1999).*
Tiira et al. (PLoS ONE, vol. 7, No. 7, e41684, Jul. 2012).*
Tacher et al. (J. of Heredity, vol. 96, No. 7, pp. 812-816, 2005).*
Downs et al. (Veterinary Ophthalmology, vol. 17, No. 2, pp. 126-130, 2014).*
Downs et al. (Canine Genetics, and Epidemiology, vol. 1, No. 4, pp. 1-12, Dec. 2014).*
Ansley et al., "Basal body dysfunction is a likely cause of pleiotropic Bardet-Biedl syndrome", Nature, vol. 425. No. 6958, pp. 628-633 (2003).
Bin et al., "BBS7 and TTC8 (BBS8) mutations play a minor role in the mutational load of Bardet-Biedl syndrome in a multiethnic population", Human Mutation, vol. 30, No. 7, pp. E737-E746 (2009).
Accession No. XM_003639207, Version XM_003639207.1, "Canis lupus familiaris tetratricopeptide repeat domain 8 (TTC8), mRNA" 2 pags (2011).
International Serch Report from PCT Patent Application No. PCT/GB2013/051365 mailed Aug. 5, 2013, application now published as PCT Publication No. WO 2013/179001 on Dec. 5, 2013.
Riazuddin et al., "A splice-site mutation in a retina-specific exon of BBS8 causes nonsyndromic retinitis pigmentosa", Amer. J. Hum. Genet., vol. 86, No. 5, pp. 805-812(2010).
Zangerl et al., "Identical mutation in a novel retinal gene causes progressive rod-cone degeneration in dogs and retinitis pigmentosa in humans", Genomics, vol. 88, No. 5, pp. 551-563 (2006).
Dekomien and Epplen, "Analysis of PDE6D and PDE6G genes for generalised progressive retinal atrophy (gPRA) mutations in dogs", Genet. Sel. Evol.; vol. 35, No. 4, pp. 445-456 (2003).
Dekomien and Epplen, "Evaluation of the canine RPE65 gene in affected dogs with generalized progressive retinal atrophy"; Mol. Vis., vol. 9, pp. 601-605 (2003).

* cited by examiner

*Primary Examiner* — Jeanine A Goldberg
(74) *Attorney, Agent, or Firm* — Judy Mohr; McDermott Will & Emery LLP

(57) ABSTRACT

The invention relates to the use of the TTC8 gene as a biomarker for the prognosis of a canine mammal developing progressive retinal atrophy. The invention also relates to in vitro methods of prognosing progressive retinal atrophy in a canine mammal by detecting a genetic variation within the TTC8 gene and to primers and prognostic kits for use in said method.

7 Claims, 6 Drawing Sheets

FIGURE 3

TTC8 AS PROGNOSTIC GENE FOR PROGRESSIVE RETINAL ATROPHY IN DOGS

CROSS REFERENCE TO RELATED APPLICATIONS

This application is a U.S. National Stage of International Patent Application No. PCT/GB2013/051365, filed May 24, 2013, which claims the benefit of priority to GB Application No. 1209420.7, filed May 28, 2012, each of which is hereby incorporated by reference in its entirety.

REFERENCE TO A SEQUENCE LISTING

A Sequence Listing is submitted with this application in the form of a text file, created Nov. 25, 2014, and titled "09174300158005seqlist.txt" (1,976 bytes), the contents of which are incorporated herein by reference in their entirety.

FIELD OF THE INVENTION

The invention relates to the use of the TTC8 gene as a biomarker for the prognosis of a canine mammal developing progressive retinal atrophy. The invention also relates to in vitro methods of prognosing progressive retinal atrophy in a canine mammal by detecting a genetic variation within the TTC8 gene and to primers and prognostic kits for use in said method.

BACKGROUND OF THE INVENTION

In animals, inherited and progressive retinal diseases are commonly referred to as progressive retinal atrophy (PRA), and are characterised by progressive retinal degeneration resulting in loss of vision. In typical PRA, rod photoreceptor responses are lost first followed by cone photoreceptor responses [1]. Fundus changes observed in PRA are bilateral and symmetrical and include tapetal hyper-reflectivity in the early stages followed by vascular attenuation, pigmentary changes and atrophy of the optic nerve head in the later stages of disease [2]. Numerous forms of PRA have been documented in more than 100 dog breeds and while they exhibit similar clinical signs, the aetiology, age of onset and rate of progression vary between and within breeds. Several disease-causing genes have been reported for some forms of PRA [3], but many remain undefined.

PRA is considered the veterinary equivalent of Retinitis Pigmentosa (RP), which is the collective name for a group of inherited human retinal disorders that leads to progressive loss of vision in approximately 1 in 4000 people [4,5,6]. Rod photoreceptor cells are predominantly affected and therefore clinical symptoms typically include night blindness and loss of peripheral vision. With disease progression the cones also degenerate resulting in central vision loss and eventually complete blindness is possible. To date, 182 genes have been shown to cause a wide spectrum of retinal disease, including RP (RetNet; www.sph.uth.tmc.edu/retnet/). Mutations in these genes currently only account for approximately 30% of recessive RP cases. [7].

Canine diseases have already proved valuable natural models for the study of many varied human conditions such as cardiac conotruncal malformations [8], myotubular myopathy [9] and hereditary retinopathies such as Leber congenital amaurosis and achromatopsia [10,11]. Further to this, canine models for human eye diseases have proved invaluable in gene-therapy studies, most notably the canine model of Leber congenital amaurosis associated with RPE65 [12, 13,14,15,16].

Most PRA cases in the Golden Retriever (GR) are clinically indistinguishable from other forms of PRA. The mode of inheritance appears from pedigree information to be autosomal recessive and the age of diagnosis is most commonly at a relatively late age of approximately 6 years.

There is therefore a great need to identify the causal genetic variant responsible for PRA in canines.

SUMMARY OF THE INVENTION

According to a first aspect of the invention, there is provided the TTC8 gene for use as a biomarker for the in vitro prognosis of progressive retinal atrophy developing in a canine mammal.

According to a further aspect of the invention, there is provided an in vitro method of prognosing progressive retinal atrophy in a canine mammal, the method comprising the step of detecting genetic variation within the TTC8 gene.

According to a further aspect of the invention, there is provided a primer pair for use in a method of prognosing progressive retinal atrophy in a canine mammal, wherein said primers are capable of amplifying all or part of the TTC8 gene, wherein the amplified region is less than 500 nucleotides in length, such as less than 300 nucleotides in length, in particular less than 200 nucleotides in length, and wherein the primers are as defined herein.

According to a further aspect of the invention, there is provided a kit for use in a method of prognosing progressive retinal atrophy in a canine mammal, wherein said kit comprises:
(a) a primer pair, wherein said primers are capable of amplifying all or part of the TTC8 gene, wherein the amplified region is less than 500 nucleotides in length, such as less than 300 nucleotides in length, in particular less than 200 nucleotides in length, and wherein the primers are as defined herein; and
(b) means for providing a test sample from the canine mammal.

According to a further aspect of the invention, there is provided a method of treating progressive retinal atrophy in a canine mammal, which method comprises assessing the progressive retinal atrophy status of a canine mammal by use of a method as defined herein and if the canine mammal is identified as affected by progressive retinal atrophy, treating said canine mammal to prevent or reduce the onset of progressive retinal atrophy.

According to a further aspect of the invention, there is provided a method of treating progressive retinal atrophy in a canine mammal, which method comprises increasing the level of non-mutant, wild-type TTC8 gene expression and/or TTC8 gene product activity in the canine mammal.

SNP genotypes for 10 PRA cases and 16 PRA controls, over the two regions identified during the GWA study. The most associated SNPs, BICF2P582923 (Marker 1) at 63.614 Mb and BICF2G630416812 (Marker 2) at 71.732 Mb, are indicated with arrows. All 10 cases and 5 controls share a 437 kb homozygous block, while 8 cases and none of the controls share a larger homozygous region (Affected haplotype) upstream of BICF2P582923 in critical region 1.

Figure 3:
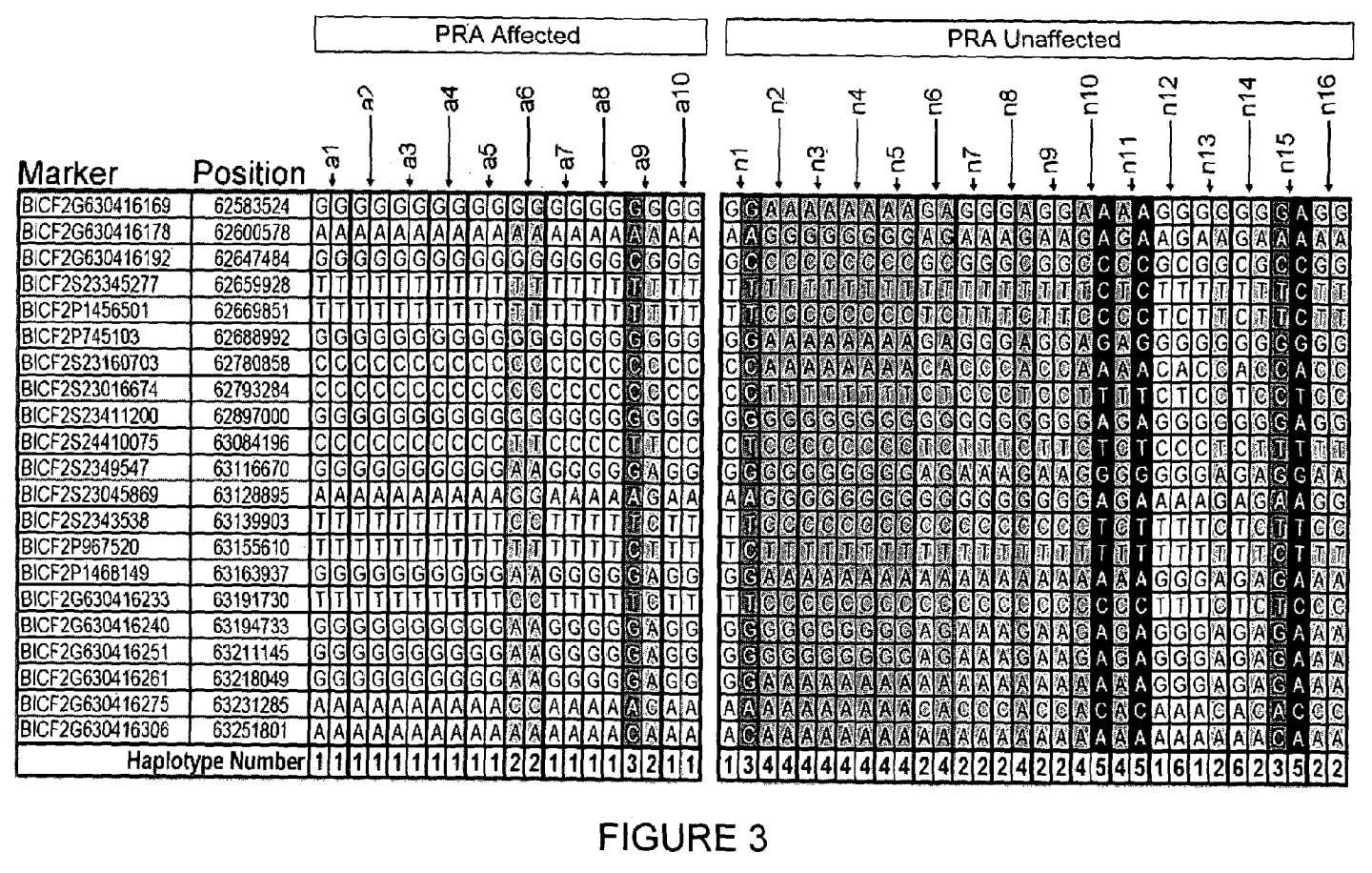

FIG. 3: Fine mapping using haplotype analysis.

SNP genotypes for 10 PRA cases and 16 PRA controls, over the 668 kb "Affected haplotype" identified during the GWA study. Inferred phasing of the 21 SNP markers revealed six unique haplotypes, each of which was assigned a colour and number. Haplotype number 1 is homozygous in 8/10 cases, but none of the controls.

Figure 4:
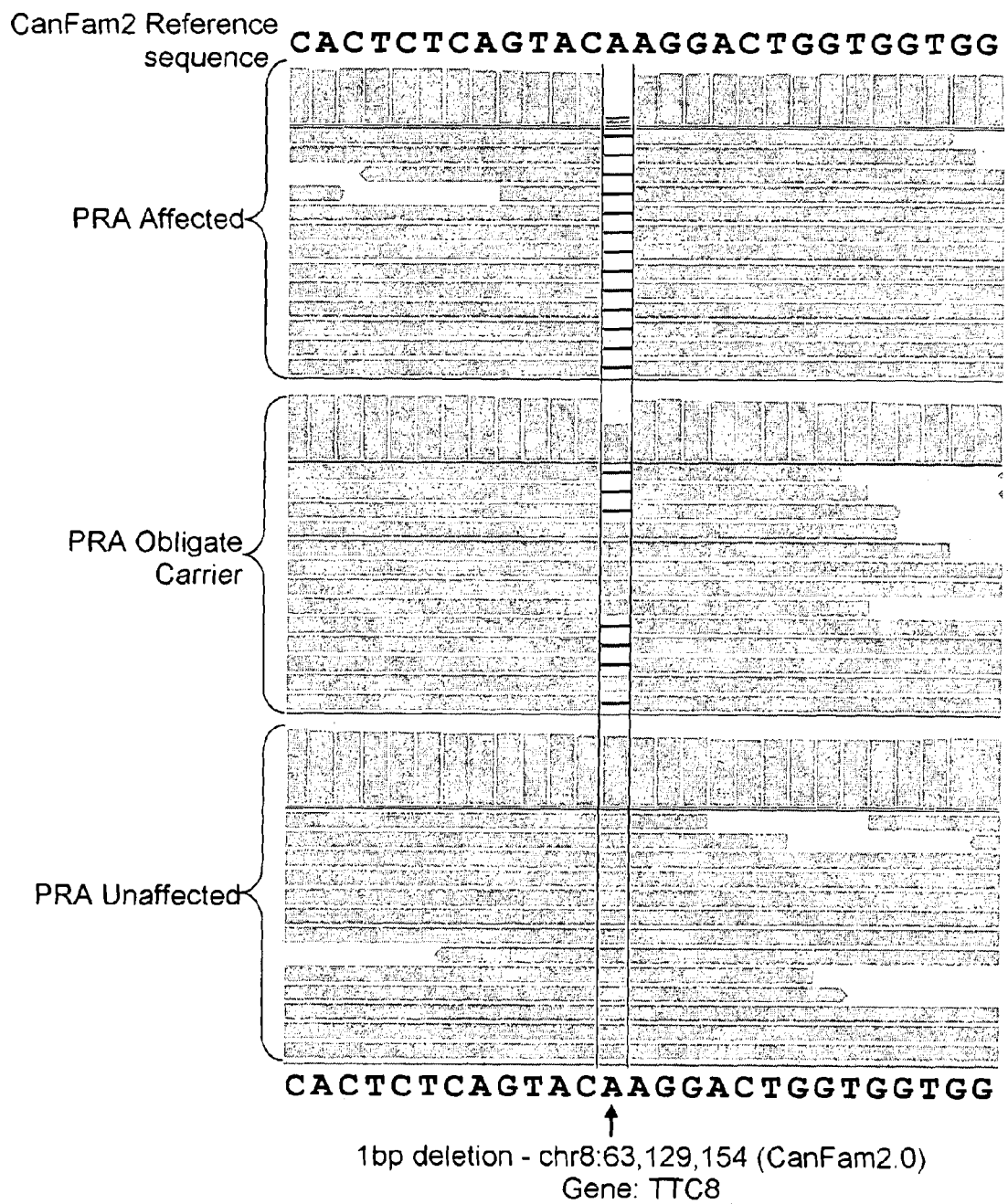

FIG. 4: IGV display of the 1-bp deletion in TTC8 (c.669delA).

Each of the three samples (PRA-affected, obligate carrier and control) viewed in IGV are represented by two panels. The upper panel is a histogram where the height of each column is representative of the read depth at that location. The lower panel is a graphical view of some of the reads that align to that location. The adenosine ("A") base indicated is absent in almost all reads in the PRA-affected sample, approximately half the reads in the obligate carrier and sample and none of the reads in the PRA-unaffected (control) sample.

Figure 5:
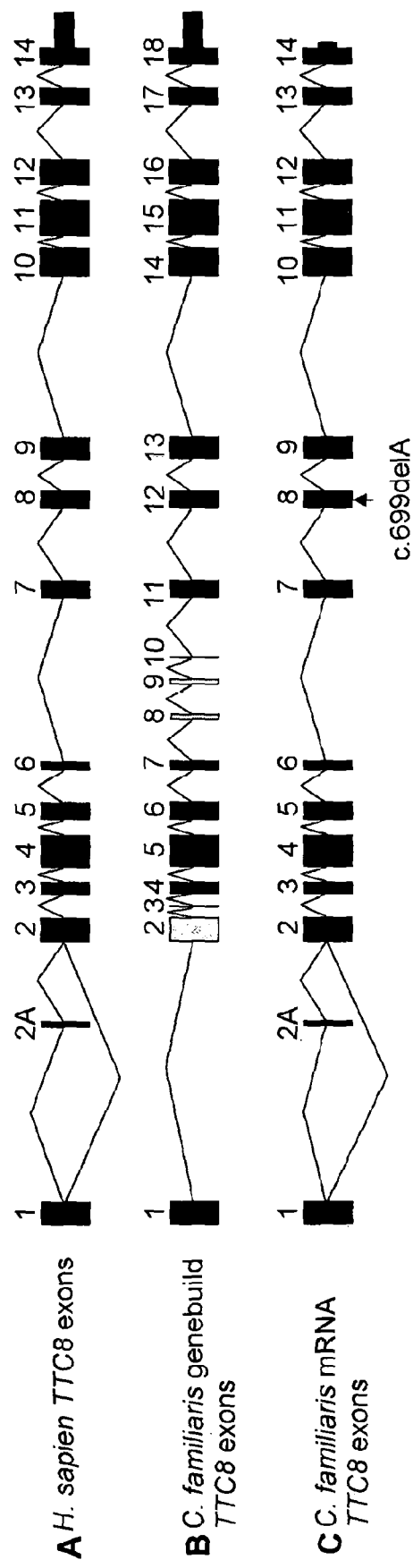

FIG. 5: Graphical comparison of the exons and exon-intron boundaries of human and canine TTC8.

A) Human (*Homo sapiens*) TTC8. B) Canine (*Canis familiaris*) TTC8 as predicted by Ensembl genebuild. Thirteen of the genebuild exons predicted are identical to the human exons (black). Exon 2 (grey) is different at the 3' exon-intron boundary. Exons 3, 8, 9 and 10 (grey) show no sequence or size similarity to their human equivalents and are probably incorrect. C) Canine TTC8 exons confirmed by sequencing the retinal mRNA transcript. Exon 2A has not been predicted by Ensembl genebuild. The location of the sequence variant is indicated.

Figure 6:
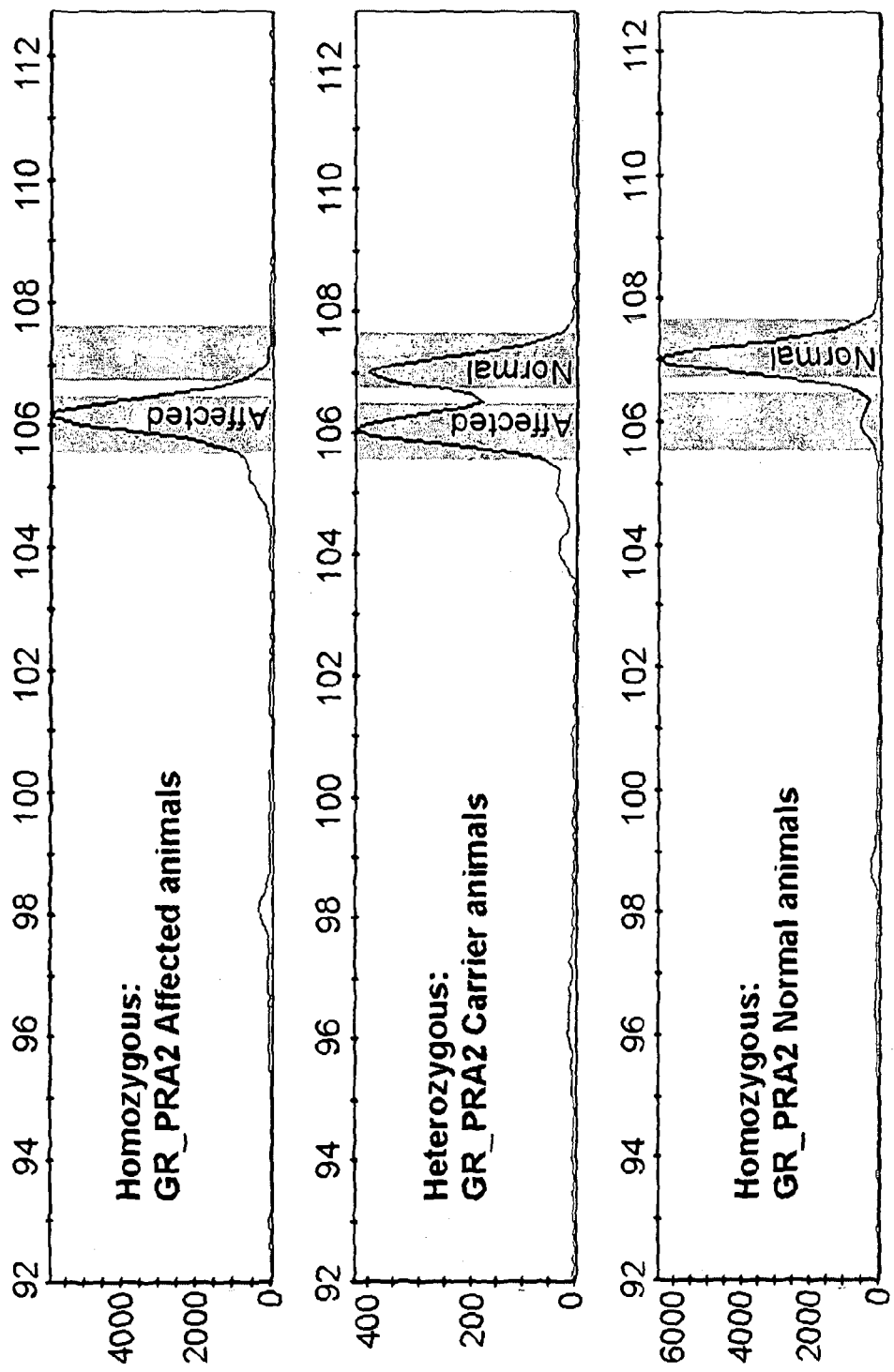

FIG. 6: Traces used for data scoring.

The traces show the peaks used for scoring sequencing data. Affected—there must be only one peak at the mutation site (size 109 for GR_PRA2). Carrier—there must be two distinct peaks. The lower peak should be at least ⅔ height of the higher peak. If it is less than ⅔ of the height then the experiment must be repeated. Normal—there must be only one peak at the mutation site (size 110 for GR_PRA2).

DETAILED DESCRIPTION OF THE INVENTION

According to a first aspect of the invention, there is provided the TTC8 gene for use as a biomarker for the in vitro prognosis of progressive retinal atrophy developing in a canine mammal.

According to a further aspect of the invention, there is provided an in vitro is method of prognosing progressive retinal atrophy in a canine mammal, the method comprising the step of detecting genetic variation within the TTC8 gene.

The present inventors have identified a genetic mutation in the canine TTC8 gene that is associated with progressive retinal atrophy in canines, such as Golden Retrievers. This newly identified mutation also has the advantage of potentially serving as a suitable animal model for human Retinitis Pigmentosa (RP), and potentially Bardet-Biedl Syndrome (BBS) as well.

In addition, the inventors have developed a genotyping-based prognostic test that can be used to determine whether a dog is clear, will potentially be affected by, or a carrier of progressive retinal atrophy. This can be used, inter alia, in selective breeding to avoid affected offspring.

It will be understood that references herein to a "prognostic test" refer to a test that can be used to predict the relative likelihood of a canine mammal developing a particular disease. Progressive retinal atrophy generally has a late onset in canines, therefore the newly identified mutation disclosed herein, has the advantage of being able to predict how likely a young canine is to develop the disease within its lifetime.

It will also be appreciated that the present invention can equally be used to diagnose a canine mammal affected by progressive retinal atrophy.

Furthermore, the inventors have devised a prognostic genotyping assay that determines the presence or absence of mutation in the canine TTC8 gene in canine DNA.

The inventors have previously identified a form of PRA, Golden Retriever PRA1 (GR_PRA1), caused by a mutation in the SLC4A3 gene that accounts for the majority (approximately 56%) of cases of PRA in the Golden Retriever breed [17]. In the closely related Labrador Retriever (LR) breed, the only known form of PRA is called progressive rod cone degeneration (prcd-PRA) [18], a form of PRA that affects at least 22 other breeds. The prcd-PRA mutation has also been associated with PRA in a small number of PRA-affected Golden Retrievers. Worldwide however, the Golden Retrievers for which PRA can be explained by the mutation in the prcd gene are in the minority [19].

Several forms of PRA are present in the Golden Retriever, including the prcd and GR_PRA1 variants, but these mutations account for approximately only 56% of cases of PRA. Using a genome-wide association (GWA) analysis approach, the inventors have identified a novel mutation in the TTC8 gene that represents a major causal locus for PRA in the Golden Retriever. This mutation appears to be fully penetrant and a common cause of PRA in the breed.

The data presented herein identifies a single base deletion mutation in TTC8, one of seven genes encoding proteins that form the Bardet-Biedl Syndrome (BBS) protein complex [20]. The mutation causes a shift in the reading frame resulting in a subsequent premature termination codon. The evidence also shows that this mutation represents a third susceptibility locus for late onset PRA, known hereafter as GR_PRA2, in Golden Retrievers.

TTC8 (a.k.a. BBS8) encodes the protein tetratricopeptide repeat domain 8 and was recognized as a candidate gene due to its previous implication in BBS and autosomal recessive RP in humans [22,23,24]. TTC8 is one of seven BBS proteins that form a stable complex known as the BBSome, which functions primarily at the ciliary membrane and is thought to play a role in ciliogenesis [20]. BBS is a pleiotropic disease and typical symptoms include obesity, retinal degeneration, kidney malformation, olfactory deficits, polydactyly and learning disabilities. While the syndrome is usually inherited in an autosomal recessive manor, triallelic inheritance has also been observed [25]. Human TTC8 is made up of 14 exons and alternative splicing of the fifth exon results in two isoforms that are widely expressed [23]. In addition, a retina-specific isoform, localized to the outer nuclear layer, is created by the alternative splicing of exon 2A [22]. While most mutations that significantly alter the structure of TTC8 cause BBS, those that result in in-frame deletion or skipping of the 10 amino acids encoded by exon 2A cause non-syndromic Retinitis Pigmentosa. The TTC8$_{c.669delA}$ variant in the Golden Retriever is predicted to have a significant effect on the structure of the protein, including the loss of all tetratricopeptide repeats near the carboxyl terminus, known to be protein-protein interaction motifs [23].

While PRA is widely considered to be the veterinary equivalent of RP, the limited characterisation of PRA at a cellular level is insufficient to fully justify this comparison. Further investigations are required to understand the cellular processes involved in this form of PRA, including whether the rod or cone photoreceptor cells are affected first and whether other signs indicative of a syndrome are present in affected dogs. Given the significant effect of the TTC8 mutation on the protein it is interesting that no other clinical signs have been reported in any of the PRA-affected dogs homozygous for this variant. It is unclear whether the phenotypic differences between human BBS and canine GR_PRA2 phenotypes are purely due to species differences or some other as yet unknown mechanism, such as the effect of modifier genes.

The surprising identification of a frameshift deletion in TTC8 in Golden Retriever dogs with PRA, establishes GR_PRA2 as a suitable model for human RP, and potentially BBS as well. This TTC8 mutation in the Golden Retriever may also prove to be a valuable model for further studies to enhance our understanding of visual pathways and gene therapy investigations.

In one embodiment, the canine mammal is a dog which is a breed selected from a Golden Retriever or a Labrador Retriever. In a further embodiment, the canine mammal is a Golden Retriever.

In one embodiment, the method defined herein comprises the steps of:
(i) providing a sample of nucleic acid from the canine mammal;
(ii) detecting genetic variation within the TTC8 gene in the nucleic acid sample; and
(iii) correlating the result from step (ii) with the prognosis of progressive retinal atrophy developing in the canine mammal.

In one embodiment, the nucleic acid is genomic DNA.

In one aspect of the invention, the method may include the step of screening a canine mammal for progressive retinal atrophy as described herein, and if the animal is identified as a carrier, selecting it for breeding with an animal which is not a carrier of progressive retinal atrophy (i.e. is clear of progressive retinal atrophy and homozygous for the non-mutant, wild-type allele). The ability to identify carriers for breeding purposes is of great importance because progressive retinal atrophy is an extremely debilitating disease which invariably leads to total blindness.

In one embodiment, the genetic variation detected by the method defined herein is within exon 8 of the TTC8 gene.

In one embodiment, the genetic variation detected by the method defined herein comprises a deletion mutation within the TTC8 gene.

In a further embodiment, the deletion mutation comprises single base deletion at position 63,129,154 on chromosome 8 (CanFam 2.0). This mutation results in the deletion of an adenine residue causing a shift in the reading frame and a premature termination codon.

Progressive retinal atrophy in dogs is an autosomal recessive condition. Thus the progressive retinal atrophy status may be selected from: clear of progressive retinal atrophy, affected by (i.e. having or likely to develop) progressive retinal atrophy, or a carrier of progressive retinal atrophy.

The individual animal tested may or may not be entirely symptomless and\or may be considered to be at risk from progressive retinal atrophy (based on pedigree etc.).

In one embodiment, the method additionally comprises the step of establishing whether or not the canine mammal is heterozygous or homozygous for the genetic variation within the TTC8 gene.

In one embodiment, if the canine mammal is homozygous for the genetic variation within the TTC8 gene, it is prognosed as a canine mammal that will suffer from progressive retinal atrophy in its lifetime.

Often, the canine mammal might not have developed progressive retinal atrophy when it is tested for the TTC8 mutation because it is a disease that usually has a mid-age onset (i.e. around 6 years old). It is particularly useful to be able to predict whether a canine mammal, such as a young canine mammal, is likely to develop the disease in its lifetime, especially for breeding purposes.

In one embodiment, if the canine mammal is heterozygous for the genetic variation within the TTC8 gene, it is selected as being suitable for breeding with a canine mammal of the same breed which is homozygous for the wild-type TTC8 gene. The identification of a canine mammal which is heterozygous for the mutation, indicates that the canine is a carrier of progressive retinal atrophy.

In one embodiment, if the canine mammal is homozygous for the wild-type TTC8 gene, it is selected as being suitable for breeding with a canine mammal of the same breed which is homozygous or heterozygous for the wild-type TTC8 gene.

The method of the invention may optionally comprise, in addition to detecting genetic variation within the TTC8 gene, the assessment from the same sample of other markers which are linked or associated with other canine disorders. Thus, in one embodiment, the sample used in the method defined herein is assessed for one or more other markers which are linked or associated with canine disorders.

Particular methods of detecting markers in nucleic acid samples are described in more detail hereinafter.

Nucleic Acid Sample

The sample from the canine mammal may be prepared from any convenient sample, for example from blood or skin tissue. In one embodiment, DNA is extracted from blood or from buccal (cheek) cells on a swab. In a further embodiment, DNA is extracted from buccal cells on a swab.

The DNA sample analysed may be all or part of the sample being obtained. Methods of the present invention may therefore include obtaining a sample of nucleic acid obtained from the canine mammal. Alternatively, the assessment of the TTC8 gene may be performed or based on an historical DNA sample, or information already obtained therefrom e.g. by assessing the TTC8 gene in DNA sequences which are stored on a databank.

It will be appreciated that the assessment may be performed using mRNA (or cDNA), rather than genomic DNA.

Genetic Variations

It will be appreciated that the genetic variations include any variation in the native, non-mutant or wild type genetic code of the TTC8 gene from said canine mammal under analysis. Examples of such genetic variations include: mutations (e.g. point mutations), substitutions, deletions, single nucleotide polymorphisms (SNPs), haplotypes, chromosome abnormalities, Copy Number Variation (CNV), epigenetics and DNA inversions.

References herein to the term "single-nucleotide polymorphism (SNP)" is intended to refer to DNA sequence variation occurring when a single nucleotide in TTC8 gene differs between members of a species or between paired chromosomes in an individual.

In one embodiment the genetic variation is a functional mutation i.e. one which is causative of progressive retinal atrophy. Mutations may be functional in that they affect amino acid encoding, or by disruption of regulatory elements (e.g., which may regulate gene expression, or by disruption of sequences—which may be exonic or intronic—involved in regulation of splicing). However it will be appreciated that other markers showing association with progressive retinal atrophy, may also have diagnostic utility and could be used in combination with the assessment of the invention.

In one embodiment, the genetic variation is a deletion mutation which causes a frameshift in the TTC8 gene. This may cause premature termination.

In one embodiment, the genetic variation is within exon 8 of the TTC8 gene.

In one particular embodiment, the genetic variation comprises a deletion mutation within the TTC8 gene. In a further embodiment, the deletion mutation comprises a single base pair deletion at position 63,129,154 on chromosome 8 (as identified in the current whole genome sequence assembly (CanFam 2.0: www.ensembl.org/Canis_familiaris/).

In one embodiment, the primers used to detect the TTC8 gene comprise:

Forward: 5'-TGCCCTTTCCACAGAGCAC-3' (SEQ ID NO: 1); and
Reverse: 5'-CCATGTCTAAGCCCTTCACAA-3' (SEQ ID NO: 2).

These give fragment amplification of:
Normal, non-mutant, wild-type=110 bp
Mutant=109 bp In one embodiment, assessment of the TTC8 gene will establish whether or not the individual animal is heterozygous or homozygous for the specific length variant in this region.

Accordingly, in one embodiment the method of the present invention comprises detecting genetic variation within the TTC8 gene in a genomic DNA sample obtained from the canine mammal as described above e.g. a deletion mutation of nucleotide 63,129,154 on chromosome 8 (as identified in the current whole genome sequence assembly (CanFam 2.0: www.ensembl.org/Canis_familiaris/).

Use of Other Polymorphisms

The genetic variation may be one which is in linkage disequilibrium with the hereinbefore mentioned deletion mutation—this may for example be a microsatellite repeat polymorphism or a single nucleotide polymorphism (SNP), which may be in an intron, exon or promoter sequence of the TTC8 gene, or located sufficiently close to the TTC8 gene to be in linkage disequilibrium with the mutation.

In one embodiment, any such polymorphism will be a common polymorphism (allele frequency >0.05). As is understood by the person skilled in the art, linkage disequilibrium is the non-random association of alleles. Further details may be found in Kruglyak (1999) Nature Genetics 22: 139, and Boehnke (2001) Nature Genetics 25: 246-247). For example, results of recent studies indicate significant linkage disequilibrium may extend to around 2 MB depending on the breed of dog (400-700 kb in Golden Retriever and Labrador Retriever, 2.4 Mb in Akita, and 3-3.2 Mb in Bernese Mountain Dog and Pekingese - see www.ncbi.nlm-.nih.qov/entrez/query.fcgi?cmd=Retrieve&db=pubmed&dopt=Abstract&list_uids=15545498&query hl=4). Thus genetic variations which are proximal to the TTC8gene and in linkage disequilibrium with the hereinbefore mentioned deletion mutation are also within the scope of the invention.

A region which is described as 'proximal' or 'sufficiently close' to a polymorphic marker may be within about 3000 kb, 2000 kb or 1000 kb of the TTC8 gene, preferably within about 500 kb away, and more preferably within about 100 kb, more preferably within 50 kb, more preferably within 10 kb of the TTC8 gene.

For these other genetic variations (e.g. SNP or microsatellite polymorphisms), the method will generally involve determining the identity of a nucleotide or nucleotides at the position of said polymorphism. In one embodiment, assessment of the SNPs at the positions described above will establish whether or not the individual is heterozygous or homozygous for the allele at these sites.

Materials

The invention further provides oligonucleotides for use in probing or amplification reactions, which may be fragments of the TTC8 gene.

Nucleic acid for use in the methods of the present invention, such as an oligonucleotide probe and/or pair of amplification primers, may be provided in isolated form and may be part of a kit, e.g. in a suitable container such as a vial in which the contents are protected from the external environment. The kit may include instructions for use of the nucleic acid, e.g. in PCR and/or a method for determining the presence of nucleic acid of interest in a test sample. A kit wherein the nucleic acid is intended for use in PCR may include one or more other reagents required for the reaction, such as polymerase, nucleotides, buffer solution etc. The nucleic acid may be labelled. A kit for use in determining the presence or absence of nucleic acid of interest may include one or more articles and/or reagents for performance of the method, such as means for providing the test sample itself, e.g. a swab for removing cells from the buccal cavity or a syringe for removing a blood sample (such components generally being sterile).

The various embodiments of the invention described above may also apply to the following: a means for prognosing progressive retinal atrophy in a canine mammal; a prognostic kit comprising such a means; and the use, in the manufacture of means for prognosing progressive retinal atrophy in a canine mammal of sequences (e.g., PCR primers) to amplify a region of the TTC8 gene as described herein.

Therapy

According to a further aspect the invention there is provided a method of treating progressive retinal atrophy in a canine mammal, which method comprises assessing the progressive retinal atrophy status of a canine mammal by use of a method as defined herein and if the canine mammal is identified as affected by progressive retinal atrophy, treating said canine mammal to prevent or reduce the onset of progressive retinal atrophy.

Gene Replacement Therapy

As noted above the present inventors have identified a mutation in exon 8 of the TTC8 gene in the DNA which changes the reading frame of the DNA, in turn introducing a 'premature stop codon' which causes the protein to be prematurely terminated.

Thus, according to a further aspect of the invention, there is provided a method of treating progressive retinal atrophy in a canine mammal, which method comprises increasing the level of non-mutant, wild-type TTC8 gene expression and/or TTC8 gene product activity in the canine mammal.

Normal (i.e. non-mutant) TTC8 gene nucleic acid sequences described above can, for example, be utilized for the treatment of progressive retinal atrophy. Such treatment can be administered, for example, in the form of gene replacement therapy. Specifically, one or more copies of a normal TTC8 gene or a portion of the TTC8 gene that directs the production of a TTC8 gene product exhibiting normal TTC8 gene function, may be inserted into the appropriate cells within a canine mammal in need of the same, using vectors that include, but are not limited to adenovirus, adeno-associated virus, and retrovirus vectors, in addition to other particles that introduce DNA into cells, such as liposomes.

Also included are methods using liposomes either in vivo, ex vivo or in vitro wherein TTC8 gene DNA is delivered to the cytoplasm and nucleus of target cells.

In another embodiment, techniques for delivery involve direct administration of such TTC8 gene sequences to the site of the cells in which the TTC8 gene sequences are to be expressed. Additional methods that may be utilized to increase the overall level of TTC8 gene expression and/or TTC8 gene product activity include the introduction of appropriate TTC8 gene expressing cells, preferably autologous cells, into the canine mammal at positions and in numbers that are sufficient to ameliorate the symptoms of progressive retinal atrophy. Such cells may be either recombinant or non-recombinant. The expression of the TTC8 gene sequences is controlled by the appropriate gene regulatory sequences to allow such expression in the necessary cell types. Such gene regulatory sequences are well known to the skilled artisan. Such cell-based gene therapy techniques are well known to those skilled in the art, see, e.g., Anderson, U.S. Pat. No. 5,399,349.

When the cells to be administered are non-autologous cells, they can be administered using well known techniques that prevent a host immune response against the introduced cells from developing. For example, the cells may be introduced in an encapsulated form which, while allowing for an exchange of components with the immediate extracellular environment, does not allow the introduced cells to be recognized by the host immune system.

Thus, for example, the invention provides a method of gene therapy one or more copies of a nucleic acid sequence as described herein (e.g. non-mutant TTC8 gene or an active variant thereof) may be inserted into the appropriate cells within the canine mammal, using vectors that include, but are not limited to adenovirus, adeno-associated virus, and retrovirus vectors, in addition to other particles that introduce DNA into cells, such as liposomes.

Example gene therapy vectors for use in the method of this invention include retroviral or episomal vectors expressing particular desired genes under the control of the promoter and/or the supplemental control sequences disclosed herein (see, e.g., Axel, et al., U.S. Pat. No. 4,399,216, and Pastan, et al., U.S. Pat. No. 5,166,059, both incorporated herein by reference). Delivery systems as contemplated herein include both viral and liposomal delivery systems (see, e.g., Davis, et al., U.S. Pat. No. 4,920,209, incorporated herein by reference). Such gene therapy vectors may incorporate targeting signals to the appropriate membrane or organ. Alternatively, or additionally cell or organelle specific promoters may be used.

The invention also provides such vectors and DNA molecules for use in a method of treatment of progressive retinal atrophy in a canine mammal.

The invention further provides use of such DNA molecules in the preparation of a medicament, for example for the treatment of a canine mammal.

Assessment of Genetic Variation

Methods for detecting or assessing genetic variations are reviewed by Schafer and Hawkins, (Nature Biotechnology (1998)16, 33-39, and references referred to therein) and include: allele specific oligonucleotide probing, amplification using PCR, denaturing gradient gel electrophoresis, RNase cleavage, chemical cleavage of mismatch, T4 endonuclease VII cleavage, multiphoton detection, cleavase fragment length polymorphism, *E. coli* mismatch repair enzymes, denaturing high performance liquid chromatography, (MALDI-TOF) mass spectrometry, analysing the melting characteristics for double stranded DNA fragments as described by Akey et al. (2001) Biotechniques 30; 358-367. These references, inasmuch as they may be used in the performance of the present invention by those skilled in the art, are specifically incorporated herein by reference.

The assessment of the genetic variation may be carried out on a DNA microchip, if appropriate. One example of such a microchip-system may involve the synthesis of microarrays of oligonucleotides on a glass support. Fluorescently-labelled PCR products may then be hybridised to the oligonucleotide array and sequence specific hybridisation may be detected by scanning confocal microscopy and analysed automatically (see Marshall & Hodgson (1998) Nature Biotechnology 16: 27-31, for a review).

Some preferred examples of such methods will now be discussed in more detail.

Use of Nucleic Acid Probes

The method of detecting or assessing the genetic variation may comprise determining the binding of an oligonucleotide probe to the nucleic acid sample. Thus, in one embodiment, the detection step of the method defined herein is performed by determining the binding of oligonucleotide probes to the nucleic acid sample, wherein the probes comprise all or part of the wild-type or mutant TTC8 gene.

The probe may comprise a nucleic acid sequence which binds specifically to a particular allele of a polymorphism and does not bind specifically to other alleles of the polymorphism. Where the nucleic acid is double-stranded DNA, hybridisation will generally be preceded by denaturation to produce single-stranded DNA. A screening procedure, chosen from the many available to those skilled in the art, is used to identify successful hybridisation events and isolated hybridised nucleic acid.

Probing may employ the standard Southern blotting technique. For instance DNA may be extracted from cells and digested with different restriction enzymes. Restriction fragments may then be separated by electrophoresis on an agarose gel, before denaturation and transfer to a nitrocellulose filter. Labeled probe may be hybridised to the DNA fragments on the filter and binding determined.

Binding of a probe to target nucleic acid (e.g. DNA) may be measured using any of a variety of techniques at the disposal of those skilled in the art. For instance, probes may be radioactively, fluorescently or enzymatically labeled.

Polymorphisms may be detected by contacting the sample with one or more labeled nucleic acid reagents including recombinant DNA molecules, cloned genes or degenerate variants thereof under conditions favorable for the specific annealing of these reagents to their complementary sequences within the relevant gene.

As is understood by those skilled in the art, a 'complement' or 'complementary' or 'reverse complement' sequence (the terms are equivalent) is one which is the same length as a reference sequence, but is 100% complementary thereto whereby by each nucleotide is base paired to its counterpart running in anti-parallel fashion i.e. G to C, and A to T or U.

In one embodiment, the lengths of these nucleic acid reagents are at least 15 to 30 nucleotides.

After incubation, all non-annealed nucleic acids are removed from the nucleic acid:gene hybrid. The presence of nucleic acids that have hybridized, if any such molecules exist, is then detected. Using such a detection scheme, the nucleic acid from the cell type or tissue of interest can be immobilized, for example, to a solid support such as a membrane, or a plastic surface such as that on a microtitre plate or polystyrene beads. In this case, after incubation, non-annealed, labeled nucleic acid reagents are easily removed. Detection of the remaining, annealed, labeled nucleic acid reagents is accomplished using standard techniques well-known to those in the art. The gene sequences to which the nucleic acid reagents have annealed can be compared to the annealing pattern expected from a normal gene sequence in order to determine whether a gene mutation is present.

Approaches which rely on hybridisation between a probe and test nucleic acid and subsequent detection of a mismatch may be employed. Under appropriate conditions (temperature, pH etc.), an oligonucleotide probe will hybridise with a sequence which is not entirely complementary. The degree of base-pairing between the two molecules will be sufficient for them to anneal despite a mis-match. Various approaches are well known in the art for detecting the presence of a mis-match between two annealing nucleic acid molecules. For instance, RNase A cleaves at the site of a mis-match. Cleavage can be detected by electrophoresing test nucleic acid to which the relevant probe or probe has annealed and looking for smaller molecules (i.e. molecules with higher electrophoretic mobility) than the full length probe/test hybrid. Other approaches rely on the use of enzymes such as resolvases or endonucleases.

Thus, an oligonucleotide probe that has the sequence of a region of the normal gene (either sense or anti-sense strand) in which polymorphisms associated with the trait of interest are known to occur may be annealed to test nucleic acid and the presence or absence of a mis-match determined. Detection of the presence of a mis-match may indicate the presence in the test nucleic acid of a mutation associated with the trait. On the other hand, an oligonucleotide probe that has the sequence of a region of the gene including a mutation associated with disease resistance may be annealed to test nucleic acid and the presence or absence of a mis-match determined. The presence of a mismatch may indicate that the nucleic acid in the test sample has the normal sequence, or a different mutant or allele sequence. In either case, a battery of probes to different regions of the gene may be employed.

As discussed above, suitable probes may comprise all or part of the TTC8 gene sequence (or reverse complement thereof), or all or part of a mutant form of the sequence (or reverse complement thereof). The mutant form may contain one or more of the genetic variations described herein.

Those skilled in the art are well able to employ suitable conditions of the desired stringency for selective hybridisation, taking into account factors such as oligonucleotide length and base composition, temperature and so on.

Suitable selective hybridisation conditions for oligonucleotides of 17 to 30 bases include hybridization overnight at 42° C. in 6×SSC and washing in 6×SSC at a series of increasing temperatures from 42° C. to 65° C. One common formula for calculating the stringency conditions required to achieve hybridization between nucleic acid molecules of a specified sequence homology is (Sambrook et al., 1989): $T_m = 81.5°$ C.$+16.6$ Log $[Na^+]+0.41$ (% G+C)$-0.63$ (% formamide)$-600/\#bp$ in duplex.

Other suitable conditions and protocols are described in Molecular Cloning: a Laboratory Manual: 2nd edition, Sambrook et al., 1989, Cold Spring Harbor Laboratory Press and Current Protocols in Molecular Biology, Ausubel et al. eds., John Wiley & Sons, 1992.

Amplification-Based Methods

The hybridisation of such a probe may be part of a PCR or other amplification procedure. Accordingly, in one embodiment the detection step is performed by amplifying all or part of the TTC8 gene.

The assessment of the genetic variation in the amplification product may then be carried out by any suitable method, e.g., as described herein. An example of such a method is a combination of PCR and low stringency hybridisation with a suitable probe. Unless stated otherwise, the methods of assessing the genetic variation described herein may be performed on a genomic DNA sample, or on an amplification product thereof.

Where the method involves PCR, or other amplification procedure, any suitable TTC8 gene PCR primers flanking the marker of interest may be used.

In one embodiment, the amplified region which the primers flank is less than 500 nucleotides, such as less than 300 nucleotides, in particular less than 200, especially 50 to 200 (e.g. 110) nucleotides in length.

In one embodiment, the detection step of the method defined herein is performed by amplifying all or part of exon 8 of the TTC8 gene, such that it encompasses nucleotide 63,129,154 on chromosome 8 (CanFam 2.0).

In one embodiment, the detection step of the method defined herein is performed by use of primers which flank and/or include nucleotide 63,129,154 on chromosome 8 (CanFam 2.0).

An oligonucleotide for use in nucleic acid amplification may be about 30 or fewer nucleotides. Generally specific primers are upwards of 14 nucleotides in length, but are suitably 15-25 inclusive, more preferably 18-20. Those skilled in the art are well versed in the design of primers for use processes such as PCR. Various techniques for synthesizing oligonucleotide primers are well known in the art, including phosphotriester and phosphodiester synthesis methods.

According to a further aspect of the invention, there is provided a primer pair for use in a method of prognosing progressive retinal atrophy in a canine mammal, wherein said primers are capable of amplifying all or part of the TTC8 gene, wherein the amplified region is less than 500 nucleotides in length, such as less than 300 nucleotides in length, in particular less than 200 nucleotides in length, and wherein the primers are as defined herein.

Suitable polymerase chain reaction (PCR) methods are reviewed, for instance, in "PCR protocols; A Guide to Methods and Applications", Eds. Innis et al., 1990, Academic Press, New York, Mullis et al., Cold Spring Harbor Symp. Quant. Biol., 51:263, (1987), Ehrlich (ed), PCR technology, Stockton Press, NY, 1989, and Ehrlich et al., (1991) Science 252: 1643-1650). PCR comprises steps of denaturation of template nucleic acid (if double-stranded), annealing of primer to target, and polymerisation.

An amplification method may be a method other than PCR. Such methods include strand displacement activation, the QB replicase system, the repair chain reaction, the ligase chain reaction, rolling circle amplification and ligation activated transcription. For convenience, and because it is generally preferred, the term PCR is used herein in contexts where other nucleic acid amplification techniques may be applied by those skilled in the art. Unless the context requires otherwise, reference to PCR should be taken to cover use of any suitable nucleic amplification reaction available in the art.

In one embodiment, "Amplified Fragment Length Polymorphism" (AFLP) may be carried out using primers devised on the basis of the sequences disclosed herein. Analysis of the products can be carried out using e.g. by gel electrophoresis, capillary electrophoresis.

In one embodiment, described in the Examples hereinafter, the region of DNA that contains the mutation is amplified using PCR and the length of the resulting fragment of DNA is measured.

Examples of results from the genotyping assay are shown below.

Sequencing

The genetic variation may be assessed or confirmed by nucleotide sequencing of a nucleic acid sample to determine the presence of the genetic variation. The identity may be determined by comparison of the nucleotide sequence obtained with the native, non-mutant, wild-type sequence.

Nucleotide sequence analysis may be performed on a genomic DNA sample, or amplified part thereof, or RNA sample as appropriate, using methods which are standard in the art.

Where an amplified part of the genomic DNA sample is used, the genomic DNA sample may be subjected to a PCR amplification reaction using a pair of suitable primers. In this way the region containing a particular polymorphism or polymorphisms may be selectively amplified (PCR methods and primers are discussed in more detail above). The nucleotide sequence of the amplification product may then be determined by standard techniques.

Other techniques which may be used are single base extension techniques and pyrosequencing.

Mobility Based Methods

The assessment of the genetic variation may be performed by single strand conformation polymorphism analysis (SSCP). In this technique, PCR products from the region to be tested are heat denatured and rapidly cooled to avoid the reassociation of complementary strands. The single strands then form sequence dependent conformations that influence gel mobility. The different mobilities can then be analysed by gel electrophoresis.

Assessment may be by heteroduplex analysis. In this analysis, the DNA sequence to be tested is amplified, denatured and renatured to itself or to known wild-type DNA. Heteroduplexes between different alleles contain DNA "bubbles" at mismatched basepairs that can affect mobility through a gel. Therefore, the mobility on a gel indicates the presence of sequence alterations.

Restriction Site Based Methods

Where an SNP creates or abolishes a restriction site, the assessment may be made using RFLP analysis. In this analysis, the DNA is mixed with the relevant restriction enzyme (i.e., the enzyme whose restriction site is created or abolished). The resultant DNA is resolved by gel electrophoresis to distinguish between DNA samples having the restriction site, which will be cut at that site, and DNA without that restriction site, which will not be cut.

Where the SNP does not create or abolish a restriction site the SNP may be assessed in the following way. A mutant PCR primer may be designed which introduces a mutation into the amplification product, such that a restriction site is created when one of the polymorphic variants is present but not when another polymorphic variant is present. After PCR amplification using this primer (and another suitable primer), the amplification product is admixed with the relevant restriction enzyme and the resultant DNA analysed by gel electrophoresis to test for digestion.

Kits

According to a further aspect of the invention, there is provided a kit for use in a method of prognosing progressive retinal atrophy in a canine mammal, wherein said kit comprises:

(a) a primer pair, wherein said primers are capable of amplifying all or part of the TTC8 gene, wherein the amplified region is less than 500 nucleotides in length, such as less than 300 nucleotides in length, in particular less than 200 nucleotides in length, and wherein the primers are as defined herein; and (b) means for providing a test sample from the canine mammal.

A kit for use in determining the presence or absence of nucleic acid of interest may include one or more articles and/or reagents for performance of the method, such as means for providing the test sample itself, e.g. a cheek swab (such components generally being sterile). Such a kit may also include instructions for use.

The following studies illustrate the invention:

Materials and Methods

Sample Processing

The diagnosis of individual dogs was determined by veterinary ophthalmologists through the BVA/KC/ISDS (British Veterinary Association/Kennel Club/International Sheep Dog Society) Eye Scheme in the UK or the Swedish Kennel Club Eye Scheme in Sweden. Cases were defined as dogs diagnosed as affected with PRA, i.e. displaying ophthalmascopic signs of PRA including tapetal hyperreflectivity and vascular attenuation. The controls used were free of inherited eye diseases of any kind, and at least 7 years old at the time of examination for the genome wide association analysis (GWAS) or any age for subsequent investigations.

Blood samples were collected into EDTA tubes and genomic DNA was either extracted manually from peripheral blood leukocytes using QIAamp DNA Blood Midi Kit (Qiagen, Hilden, Germany) or automatically on a QIAsymphony SP/AS instrument (Qiagen, Hilden, Germany). DNA was also extracted from whole blood using a Nucleon Genomic DNA Extraction Kit (Tepnel Life Sciences, Manchester, UK), according to the manufacturer's instructions. For samples collected as buccal mouth swabs, DNA was extracted using a QIAamp® DNA Blood Midi Kit (Qiagen, West Sussex, UK). A canine retinal tissue sample from a dog of unknown breed and free of PRA was taken post mortem, with the owner's consent. RNA was extracted using an RNeasy Protect Mini Kit (Qiagen, West Sussex, UK) according to the manufacturer's instructions.

Prcd-PRA and GR_PRA1 Screening

DNA was genotyped from 33 PRA-affected Golden Retrievers for the prcd and GR_PRA1 mutations. The former was performed using the TaqMan allelic discrimination technique (Applied Biosystems Inc., Foster City, CA) according to the manufacturer's instructions. Primers (Forward: 5'-GGCCTTTCTCCTGCAGACT-3' (SEQ ID NO: 3);

Reverse: 5'-CAGCTTCTCACGGTTGGAC-3' (SEQ ID NO: 4)) and PrimeTime Dual-Labelled Probes (G-probe: 5'-FAM-AGCCATGTGCACCACCCTCT-BHQ-3' (SEQ ID NO: 5) and C-probe: 5'-HEX-TGAGCCATGTACACCAC-CCTCT-BHQ-3' (SEQ ID NO: 6); IDT, Glasgow, UK) were designed with the Primer3 web interface primer3.sourceforge.net/) [26]. PCR amplification and allelic discrimination plate read and analysis were carried out on a Techne Quantica Real Time Thermal Cycler with the Quansoft software (Bibby Scientific Limited, Staffordshire, UK). The latter was performed by PCR amplification using fluorescent primers (Forward: 5'-6-FAM-AGCAAC-CTTGTAACCCGTA-3' (SEQ ID NO: 7) and Reverse: 5'-GGAAGAAGGCAATGAGAAAGG-3' (SEQ ID NO: 8); IDT, Glasgow, UK) and subsequent fragment length polymorphism detection using an ABI 3130xl DNA Analyzer and GeneMapper® Software (Applied Biosystems, Inc., [ABI], Foster City, Calif.).

Genome-Wide Association Mapping

CanineHD BeadChips (Illumina) were used to obtain genotype calls for 173,662 single nucleotide polymorphisms (SNPs) using DNA from 10 Golden Retriever PRA cases and 16 Golden Retriever controls and genome-wide association (GWA) analysis was conducted using the software package PLINK [27]. After removing SNPs with a minor allele frequency<5% and missing genotype calls>10% from the analysis, a final data set of 103,264 markers remained. Sample call rate was >99.7% for all samples. Identity-by-state (IBS) clustering and CMH meta-analysis with PLINK were used to examine and adjust for population stratification. As a correction for multiple testing, we repeated the GWA analyses using the Max(T) permutation procedure in PLINK (100,000 permutations, denoted by $P_{genome}$). Haplotype phases were inferred using PHASE [28]. Visual inspection of SNP genotypes and haplotypes across the region was performed to define a homozygous critical region.

DNA and mRNA Sequencing

Genomic DNA (3 µg) from 10 Golden Retriever dogs (five PRA-affected, two obligate carrier and three PRA-clear) was used to prepare libraries for sequencing. Initial shearing of genomic DNA was undertaken by The Eastern Sequence and Informatics Hub (EASIH, University of Cambridge).

Paired-end sequencing resulting in 51-bp reads was conducted in a single lane on an Illumina HiSeq 2000, by the High Throughput Group (HTG) at the Welcome Trust Centre for Human Genetics, University of Oxford, UK.

The exon-intron boundaries of canine TTC8 and SPATA7 were defined by producing ClustalW [29] alignments using the Ensembl predicted canine transcripts (TTC8: ENSCAFG00000017478; SPATA7: ENSCAFG00000017354) and available known mouse (TTC8: ENSMUSG00000021013; SPATA7: ENSMUSG00000021007) and human (TTC8: ENSG00000165533; SPATA7: ENSG00000042317) Ensembl transcripts. Primer3 [26] was used to design primers in the exons for the amplification of cDNA as well as to design primers in introns seven and eight for the amplification and sequencing of TTC8 exon 8 in genomic DNA (Table 1).

TABLE 1

GR_PRA2 genotypes and PRA clinical status for 475 Golden Retrievers

| | PRA Clinical Status | | | | |
|---|---|---|---|---|---|
| Genotype | PRA Case | PRA Carrier | Clear | Unknown UK | Total |
| TTC8$^{-/-}$ | 22 (66.7%) | 0 (0%) | 0 (0%) | 0 (0%) | 22 |
| TTC8$^{+/-}$ | 1 (3.0%) | 2 (40.0%) | 10 (3.2%) | 3 (2.4%) | 16 |
| TTC8$^{+/+}$ | 10 (30.3%) | 3 (60.0%) | 300 (96.8%) | 124 (97.6%) | 437 |
| Total | 33 | 5 | 310 | 127 | 475 |

The wild-type allele is represented by "+" and the mutant allele is represented by "−".

SPATA7 and TTC8 mRNA sequence was amplified by reverse-transcriptase PCR using SuperScript®II Reverse Transcriptase (Invitrogen) according to the manufacturer's instructions. To further investigate the remaining variant ($TTC8_{c.669delA}$) in a larger dataset, exon 8 of TTC8 was sequenced in the 26 Golden Retrievers used in the GWAS. The variant was analysed for association with PRA and compared with the most associated SNP markers, BICF2P582923 and BICF2G630416812, using the software package PLINK [27]. Exon 8 of TTC8 was amplified by polymerase chain reaction (PCR) using HotStarTaq Plus DNA Polymerase (Qiagen) in genomic DNA from the 26 Golden Retrievers that were included in the GWA study. PCR products were purified using Multiscreen HTS-PCR filter plates (Millipore). Amplification products were sequenced on an ABI 3130xl DNA Analyzer using BigDye Terminator v3.1 (Applied Biosystems) and sequence traces were assembled, analyzed and compared using the Staden Package [30].

Mutation Screening

The suggestive causative mutation for GR_PRA2 in exon 8, $TTC8_{c.669delA}$, was screened in 475 Golden Retrievers by PCR amplification using fluorescent primers (Forward: 5'-6-FAM-TGCCCTTTCCACAGAGCAC-3' (SEQ ID NO: 1) and Reverse: 5'-CCATGTCTAAGCCCTTCACAA-3' (SEQ ID NO: 2); IDT, Glasgow, UK) and subsequent fragment length polymorphism detection using an ABI 3130xl DNA Analyzer and GeneMapper® Software (Applied Biosystems, Inc., [ABI], Foster City, Calif.). The panel of 475 Golden Retrievers of any age (including the 26 DNA samples already sequenced), was made up of 33 PRA cases, 5 obligate carriers, 310 clear dogs and 127 dogs representative of the UK population. The latter group of 127 dogs were of breeding age, between one and eight years of age, had unknown PRA clinical status and were largely unrelated at the parent level (from 127 different dams and 88 different sires). In addition, samples from 177 dogs representing three breeds that are closely related to the Golden Retriever breed were also included in the mutation screening.

Results

Prcd-PRA and GR_PRA1 Screening

All dogs displaying some or all of the clinical signs typical of PRA, including a hyper-reflective tapetum and attenuated blood vessels, were diagnosed as affected with PRA.

To exclude the possibility that the affected Golden Retrievers were positive for the mutations already known to cause prcd-PRA or GR_PRA1, all 33 of the Golden Retriever cases were investigated for the previously described, autosomal recessive prcd-PRA mutation [18] and GR_PRA1 mutation [17]. None of the affected Golden Retrievers tested were found to be homozygous for the either of these mutations. A single individual was heterozygous for the prcd-PRA mutation and six were heterozygous for the GR_PRA1 mutation, while the remaining 26 were homozygous for the wild-type (normal) alleles at both loci.

Genome-Wide Association Mapping

Figure 1:
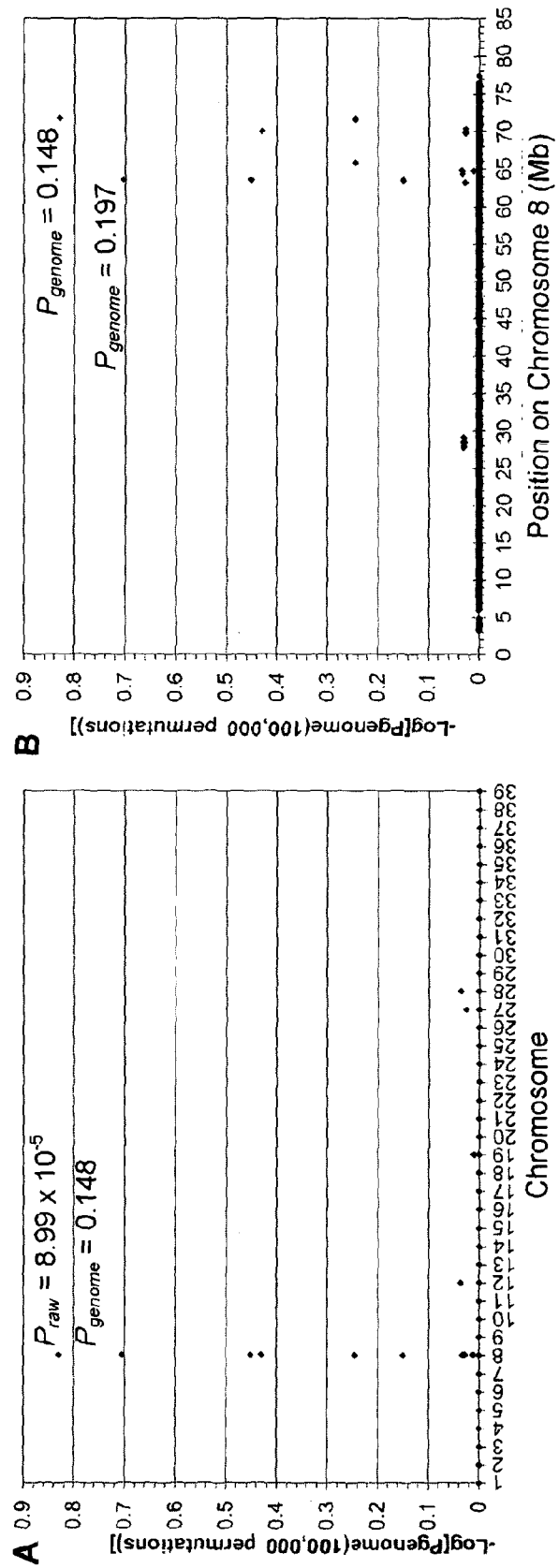
FIG. 1: Genome-wide association mapping of PRA in Golden Retrievers.
$-\text{Log}_{10}$ of p-values after correction for multiple testing and population stratification with 100 000 permutations and IBS clustering, respectively. A) $-\text{Log}_{10}$ plot of genome-wide association results show a single, albeit not statistically significant, signal on CFA8 ($P_{raw}=8.99\times10^{-5}$, $P_{genome}=0.148$). CFA39 represents the X chromosome. The most significant of the raw and permuted values are indicated. B) The associated SNPs on CFA8 form two distinct signals with the most associated SNPs at 63.614 Mb and 71.732 Mb. Permuted values at these loci are indicated.

Genome-wide association analysis of genotyping data from 26 Golden Retriever dogs, 10 cases and 16 controls (all but two of which were over the age of seven years when last examined), genotyped with 103,264 SNPs revealed a genome-wide significant association on chromosome 8 (CFA8; $p_{raw}=1.303\times10^{-6}$, $p_{genome}=0.036$). IBS clustering using genome-wide SNP marker data confirmed the presence of population stratification with a genomic inflation factor>1 ($\lambda=1.32$). The signal on CFA8 remained the strongest signal ($p_{raw}=8.99\times10^{-5}$) after correction for this by analysing for association with a CMH meta-analysis (FIG. 1), although the signal dropped below the level of significance after correcting for multiple testing ($p_{genome}=0.148$; FIG. 1). The associated region on CFA8, nevertheless remained the only associated region observed anywhere on the genome (FIG. 1) and extended from 63.600 to 71.732 Mb with the most significantly associated SNP, BICF2G630416812 ($p_{genome}=0.148$) at 71.732 Mb. Further investigation of the signal on CFA8 revealed that it was formed by two apparently independent and distinct signals at 63.614 Mb (BICF2P582923; $p_{raw}=1.16\times10^{-4}$; $p_{genome}=0.197$) and 71.732 Mb (BICF2G630416812; $p_{raw}=8.99\times10^{-5}$; $p_{genome}=0.148$) respectively (FIG. 1). These SNPs are hereafter referred to as Marker one and Marker two respectively.

Halotype and Homozygosity Analysis

Figure 2:
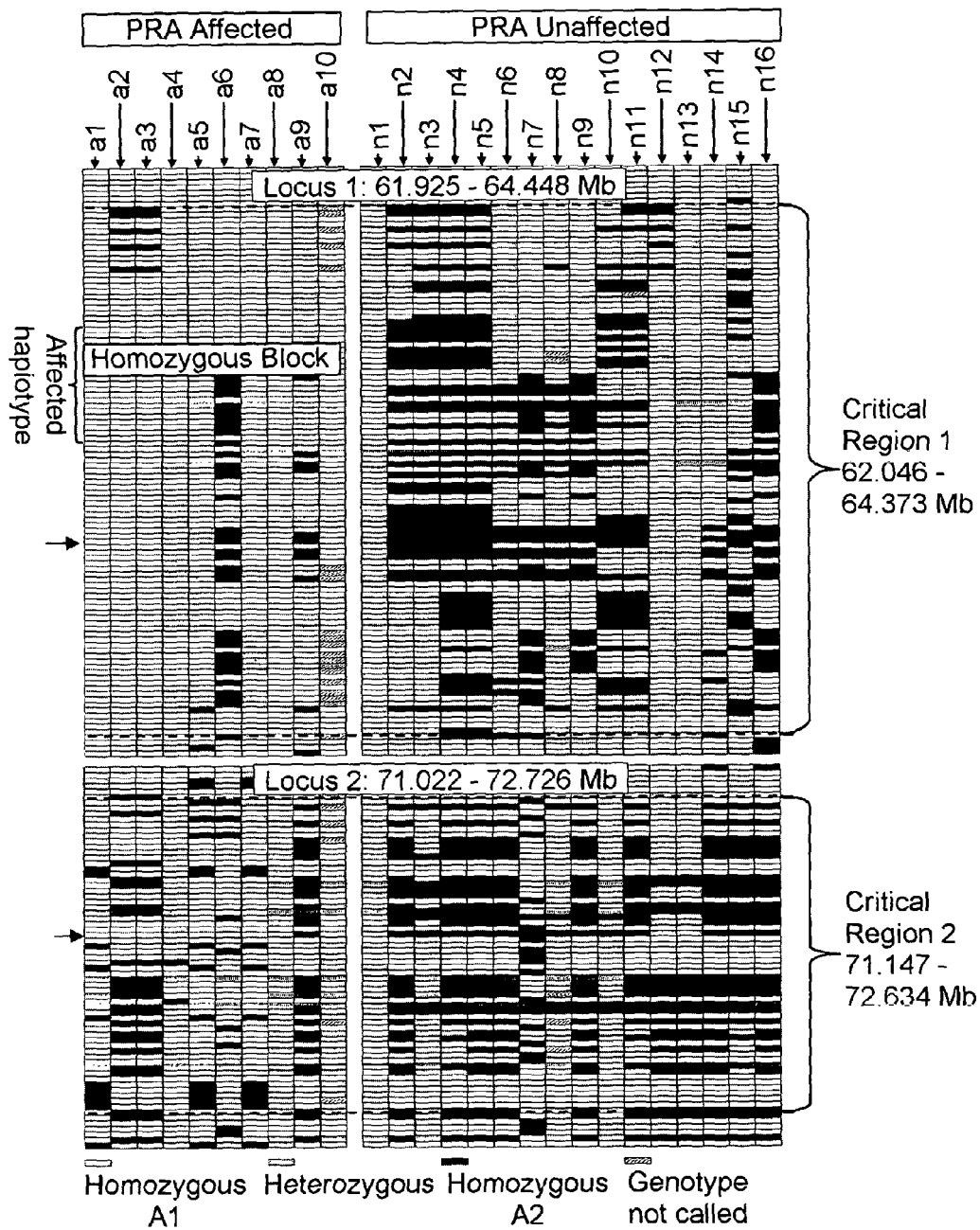
FIG. 2: Critical region definition using homozygosity analysis.

A haplotype around either Marker one or Marker two that was homozygous in all cases but not controls could not be identified through SNP homozygosity analysis. A 437 kb region was identified upstream of Marker one on CFA8 from 62.647 to 63.084 Mb for which all of the PRA cases analysed were homozygous (FIG. 2). However, five of the controls were also homozygous for the "affected" haplotype in this region. There does appear to be a larger region over which the haplotypes of most of the cases are different from those of the controls. Inferred phasing of 21 SNP markers spanning 668 kb revealed the presence of six alleles, only one of which was homozygous in 8/10 cases but none of the controls ("Affected Haplotype" in FIG. 2; Haplotype number 1 in FIG. 3). While it is possible this is the "PRA" allele, the possibility that the observed inheritance pattern of this haplotype is a coincidence and the PRA-causing mutation is actually near Marker one or two could not be discounted. Therefore critical regions were defined at these loci that have a broad margin for error and extend from 62.046 to 64.373 Mb and 71.147 to 72.634 Mb, defining regions of 2.327 and 1.487 Mb respectively, and 3.814 Mb in total. Critical region one contains 17 genes, 14 of which have human orthologues. Critical region two contains 11 genes, all of which have human orthologues.

Sequencing

To identify potential disease-causing mutations we undertook targeted resequencing of both critical regions. Repetitive DNA elements, making up approximately 40% of the regions, were masked during the design of custom RNA baits and as a result approximately 60% of the 3.814 Mb critical region was enriched and sequenced. Using 10 samples (five affected, two obligate carrier and three normal dogs) we identified more than 25,000 SNPs and 2,400 indels when compared with the CanFam2 reference sequence. Of these 666 SNPs and 168 indels segregated with the phenotype. Two provocative mutations were identified that were predicted to alter the protein product. One was a non-synonomous substitution in exon 12 of the SPATA7 gene (CFA8: 62,735,867 bp; c.1378A>G), resulting in a missense mutation (p.Thr459Ala). The other provocative mutation was a single base (adenine) deletion in exon 8 of TTC8 (CFA8: 63,129,154; c.669delA; FIG. 4), causing a shift in the reading frame and a premature termination codon (p.Lys223Argfs15).

Transcript Evaluation

All of the coding sequence of the SPATA7 and TTC8 retinal transcripts were successfully sequenced in a healthy dog revealing that both genes are transcribed in the canine retina. The presence of the SPATA7 variant, c.1378A>G, in the healthy retinal mRNA transcript as well limited conservation in 35 eitherian mammals (data not shown) suggest the variant is unlikely to be pathogenic and it was therefore eliminated from further investigation. In addition, the results show that two isoforms of TTC8 are transcribed in the canine retina and intron-exon boundaries are identical to those of the human (FIG. 5), which is in conflict with the boundaries predicted by Ensembl genebuild for the canine gene.

The full 5' and 3' UTRs for any isoform were unable to be sequenced. From the sequencing of the retinal mRNA transcripts of both isoforms we discovered that canine TTC8 (Genbank Accession No. JQ941743) contains 515 amino acids and $TTC8_{2A}$ (Genbank Accession No. JQ941742) contains 505 amino acids, with molecular weights of 58.247 kDa and 57.571 kDa respectively, predicted using the ExPASy Proteomics Server [21].

Mutation Screening

All of the 26 Golden Retriever dogs (10 cases and 16 controls) that participated in the genome-wide association study were screened for the coding variant, c.669delA, to confirm the association of this variant with PRA and compare it with the most associated SNP markers, Marker 1 and Marker 2. The variant showed significant allelic association with PRA ($P_{raw}=6.31\times10^{-7}$, $P_{genome}=0.019$) and was more strongly associated than Marker 1 at 63.614 Mb ($P_{raw}=5.79\times10^{-6}$, $P_{genome}=0.109$) or Marker 2 at 71.732 Mb ($P_{raw}=1.30\times10^{-6}$, $P_{genome}=0.037$). Eight out of ten PRA cases and none of the controls were homozygous for $TTC8_{669delA}$. While the variant shows incomplete association with PRA, it has a strong likelihood of a deleterious effect on the protein. In addition, the nucleotide and the amino acid affected by c.669delA is conserved in 32 eutherian mammals (data not shown). Analysis of the segregation of c.669delA with PRA in a family of Swedish ancestry (data not shown) indicates that GR_PRA2 is recessive and fully penetrant.

459 additional Golden Retriever dogs were screened (23 PRA affected, 299 unaffected dogs of any age and 127 dogs of unknown clinical status) making a total of 475 Golden Retrievers tested for the c.669delA variant (Table 1), to confirm that the mutation is not a commonly occurring polymorphism in this breed. Of the 33 PRA cases used in the study 22 (66.7%) were homozygous for the c.669delA mutation ($TTC8^{-/-}$) and all 315 dogs known to be clinically free of PRA at their last eye examination, including five obligate carriers of PRA, were either carriers of the mutant allele (3.8%; $TTC8^{+/-}$) or homozygous for the wild-type allele (96.2%; $TTC8^{+/+}$). The 127 samples with unknown PRA clinical statuses were all from the United Kingdom and largely unrelated at the parent level. Of these none were homozygous for the c.669delA mutation ($TTC8^{-/-}$), is three were carriers (2.2%; $TTC8^{+/-}$) and 134 were homozygous for the wild-type allele (97.8%; TTC8$^{+/+}$), resulting in a mutant allele frequency of 1.2% in the UK Golden Retriever population.

To determine whether c.669delA is associated with PRA in related breeds we screened a further 177 dogs from three closely related breeds most likely to share polymorphisms with the Golden Retriever, 48 Chesapeake Bay Retrievers (CBR), 59 Flat-Coat Retrievers (FCR) and 70 Labrador Retrievers (LR), including 18 Labrador Retrievers with non-prcd-PRA. One Labrador Retriever with PRA was homozygous for the mutation (TTC8$^{-/-}$). The remaining 69 Labrador Retriever, 45 Chesapeake Bay Retriever and 59 Flat-Coat Retriever dogs were homozygous wild-type (TTC8$^{+/+}$).

DISCUSSION

Sequencing of SPATA7 and TTC8 from healthy retinal mRNA served four purposes: 1. It confirmed the presence of both mRNA transcripts in the normal canine retina. 2. The presence of the SPATA7$_{c.1378A>G}$ variant in healthy mRNA allowed the elimination of this variant from further investigation. 3. It revealed that the exon-intron boundaries predicted by genebuild for TTC8 in the dog are incorrect for five exons. They are instead identical to the human and mouse boundaries. 4. It revealed an exon orthologous to human exon 2A, that is absent from the Ensembl canine prediction (FIG. 5). As is the case in humans and mice, canine TTC8 is alternatively spliced to produce two isoforms (TTC8 and TTC8$_{2A}$). The precise functional difference between the two isoforms is unknown, but it is thought TTC8$_{2A}$ plays in important role in the function of the protein in the photoreceptor cell-containing outer nuclear layer of the retina [22].

In order to further test the validity of the insertion mutation, 348 Golden Retrievers for the mutation were screened (Table 1). It was found that 66.7% of the PRA cases, 40% of the obligate PRA carriers and 100% of clinically unaffected dogs (which could be clear of the mutation or carry a single copy) have TTC8 genotypes that are concordant with their clinical status. All 22 dogs homozygous for the mutation i.e. TTC8$^{-/-}$, have developed PRA, suggesting that the mutation is fully penetrant, or nearly so. The inheritance observed in a family of eight dogs (three cases) is supportive of a recessive mode (data not shown). The presence of the variant in Golden Retriever dogs from countries including the USA, UK, France and Sweden suggests the variant may have arisen prior to the geographic dispersion of the breed. The mutant allele frequency of approximately 1.2% indicates that only 1 in 7000 Golden Retrievers in the UK is affected with this form of PRA, although 1 in 43 are expected to carry the mutant gene. There is a group of dogs with genotypes discordant with their phenotypes, comprising 11 PRA-affected dogs that are not homozygous for TTC8$_{c.669delA}$ and three obligate carriers do not carry TTC8$_{c.669delA}$. It is formally possible that the mutation has a dominant mode of inheritance with incomplete penetrance, or complex trait or compound heterozygote effects. However, given that three distinct loci have now been implicated in PRA in the breed, it is more likely that still more loci are responsible for the discordant cases.

The absence of the mutant TTC8 allele from Flat-Coat Retriever and Chesapeake Bay Retriever dogs tested, including some dogs affected with PRA, indicates that the mutation is rare and probably confined to the Golden Retriever breed for the most part. Identification of a Labrador Retriever (with clinically apparent PRA) homozygous for the variant suggests it may be present in the Labrador Retriever breed as well. Only 1/18 Labrador Retriever PRA cases, all of which have previously tested clear for prcd, is caused by the TTC8 variant.

PRA caused by the mutation described herein has an average age at diagnosis of 4.51 years and this is indicative of a late age of onset (data not shown). The discordant Golden Retriever PRA cases i.e. TTC8$^{+/+}$ and TTC8$^{+/-}$ tended to develop PRA at a later age, with an average age at diagnosis of 6.51 years (data not shown), which is consistent with the segregation of a fourth form of PRA in the Golden Retriever breed.

Detailed Experimental for PRA Prognostic Method

The following protocol is a further illustration of the invention, for example the procedure for use with a kit:

Specimen

Genomic DNA isolated from buccal swabs is collected from test subjects.

Equipment/Reagents

Equipment

| | |
|---|---|
| Vortex mixer | |
| Thermal cycler | MJ Tetrad - Bio Rad T100 |
| Centrifuge | MSE Microcentaur centrifuge for single columns |
| | Eppendorf 5804 centrifuge for plates |
| Heating block at 95° C. | |
| Genetic analyser | ABI 3130xl DNA Analyser |
| Gilson pipettes | |
| Computer | Software: GeneMapper |

Materials
  1.5 ml microfuge tube
  Fisherbrand PCR Plate 96 well plate
  Axygen Microplate PCR-96-FLT-C
  Alphalabs thermal sealing film
  ABI 3130 plate base
  ABI 3130 plate septum
  ABI 3130 plate retainer Reagents
  Taq Polymerase—Qiagen HotStar Taq Plus DNA Polymerase
  Reaction Buffer—Qiagen 10× reaction buffer
  dNTP solution (1.5 mM dATP, 1.5 mM dCTP, 1.5 mM dGTP, 1.5 mM dTTP)
  Primers (see SEQ ID NOs: 1 and 2)
  Deionised water
  ABI GeneScan Size Standard—400HD ROX (Applied Biosystems)
  Hi-Di formamide (Applied Biosystems)
  Ice Procedure Creating the Plate Record Create a plate record in an appropriate spreadsheet format, such as using an Excel file. The record should contain details on the samples to be included on a plate, their position on the plate, and run details for the ABI 3130xl.

Example run details for the ABI 3130xl to be included on the plate record may be as follows:

ABI 3130xl Instrument Protocol 1

| | |
|---|---|
| Dye set | D |
| Run Module | 100, Data, geno-D-10s |
| Analysis Module | GS400HDAnalysis.gsp |

Polymerase Chain Reaction (PCR)

Thaw reagents at room temperature—vortex mix excluding Taq DNA polymerase. Make a master mix for the number of samples to be tested, including three control samples (one carrier positive and 2× deionised water), in 1.5 ml microfuge tube. For each sample, aliquot master mix as detailed in Table 2.

TABLE 2

PCR Master Mix

| Component | Volume (ml) |
| --- | --- |
| 10× reaction buffer | 1.20 |
| 1.5 mM dNTP | 1.60 |
| Forward primer (10 ng/µl) | 0.05 |
| Reverse primer (10 ng/µl) | 0.05 |
| Taq Polymerase buffer | 0.12 |
| Deionised water | 6.89 |

Aliquot 10 µl of master mix wells on Fisherbrand PCR Plate 96 well plate. The Master Mix should be aliquotted into the plate before the sample to prevent contamination. Add 2 µl genomic DNA template or control samples respectively to each. The standard thermo cycling programme is given in Table 3.

TABLE 3

PCR Cycling programme

| Step | Temperature (° C.) | Time |
| --- | --- | --- |
| 1 | 94 | 10 minutes |
| 2 | 94 | 1 minute |
| 3 | 60 | 1 minute |
| 4 | 72 | 2 minutes |
| 5 | — | Go to step (2) 29 times |
| 6 | 72 | 10 minutes |
| 7 | 12 | ∞ |

PCR Product Size Analysis

After the PCR program has finished, centrifuge at 1000 rpm briefly with Eppendorf centrifuge. Add 40 µl Genescan ROX size standards to 960 µl HiDi Formamide, vortex mix and spin to consolidate all liquid at the bottom of the tube. Aliquot 10 µl into each well of a new Axygen Microplate PCR-96-FLT-C. Aliquot 1 µl of sample into the corresponding well of the plate. Seal plate with thermal film.

Heat to 95° C. for approximately 3 minutes on the heating block. Transfer quickly to ice. The plate can be stored in the fridge for up to 24 hours. Place plate in plate base, checking orientation so that the well numbers of the plate align with those of the base. Put on 3130 plate septum and clip on plate retainer. Place in holder in ABI 3130.

Load the plate record in the ABI 3130 Data Collection Software. The software Genemapper is used for the interpretation of results. The position of the normal and mutant alleles are:

Normal allele—110 bp
Mutant allele—109 bp

If there are 2 distinct peaks indicating the subject is a carrier, the smaller peak must be at least two thirds the height of the larger peak, otherwise the experiment should be repeated.

All data will be scored automatically by the GeneMapper software, but it is recommended that the data is then checked and rescored/scored manually and independently by two individuals. The second scorer will be bling to the first score. By doing this all results will be validated by a second person, which will ensure that scoring is reliable and valid.

Once all the alleles have been checked and called, export the results in the genotypes table and continue with inputting results into dog disease database, entering results and issuing certificates.

Quality Control

The negative controls with deionised water should show no peaks. It is recommended that two negative controls are run with each sample plate, i.e. 2 wells will have the DNA sample replaced with deionised water. If negative controls show significant signal the plate is void and the PCR must be repeated.

Positive controls are for information only. It is recommended that 3 positive controls (i.e. 1 normal, 1 carrier, 1 affected) are processed with each plate. The plate will be rejected and repeated if any of the positive controls are wrong, but not if they are missing or fail to be read.

Positions of positive peaks are given below:

Normal—one peak at 110 bp
Carrier—one peak at 110 bp and one peak at 109 bp
Affected—one peak at 109 bp Results The above experimental was used to diagnose 65 samples with known phenotypes in order to validate the prognostic method. Data for the samples was scored independently by four individuals. The data was then compared and all results matched between the four result readers. All samples gave results that were consistent with the sequencing data. FIG. 6 shows a trace of the peaks seen for GR_PRA2 in affected, carriers and normal animals.

REFERENCES

1. Parry H B (1953) Degenerations of the dog retina. II. Generalized progressive atrophy of hereditary origin. *Br. J. Ophthalmol.* 37: 487-502.
2. Petersen-Jones S (2005) Advances in the molecular understanding of canine retinal diseases. *J. Small Anim. Pract.* 46: 371-380.
3. André C, Chaudieu G, Thomas A, Jongh O, Jegou J P, et al. (2008) Hereditary retinopathies in the dog: Genetic fundamentals and genetic tests. *Pratique Médicale et Chirurgicale de l'Animal de Compagnie* 43: 75-84.
4. Grondahl J (1987) Estimation of prognosis and prevalence of retinitis pigmentosa and Usher syndrome in Norway. *Clin. Genet.* 31: 255-264.
5. Haim M, Holm N V, Rosenberg T (1992) Prevalence of retinitis pigmentosa and allied disorders in Denmark. I Main results. *Acta Ophthalmol.* (Copenh) 70: 178-186.
6. Pagon R A (1988) Retinitis pigmentosa. *Surv. Ophthalmol.* 33: 137-177.
7. Daiger S P, Bowne S J, Sullivan L S (2007) Perspective on genes and mutations causing retinitis pigmentosa. *Arch. Ophthalmol.* 125: 151-158.
8. Patterson D F, Pexieder T, Schnarr W R, Navratil T, Alaili R (1993) A single major-gene defect underlying cardiac conotruncal malformations interferes with myocardial growth during embryonic development: studies in the CTD line of keeshond dogs. *Am. J. Hum. Genet.* 52: 388-397.
9. Beggs A H, Bohm J, Snead E, Kozlowski M, Maurer M, et al. (2010) MTM1 mutation associated with X-linked myotubular myopathy in Labrador Retrievers. *Proc. Natl Acad. Sci. USA* 107: 14697-14702.
10. Sidjanin D J, Lowe J K, McElwee J L, Milne B S, Phippen T M, et al. (2002) Canine CNGB3 mutations establish cone degeneration as orthologous to the human achromatopsia locus ACHM3. *Hum. Mol. Genet.* 11: 1823-1833.

11. Mellersh C S, Boursnell M E, Pettitt L, Ryder E J, Holmes N G, et al. (2006) Canine RPGRIP1 mutation establishes cone-rod dystrophy in miniature longhaired dachshunds as a homologue of human Leber congenital amaurosis. *Genomics* 88: 293-301.

12. Howell J M, Fletcher S, Kakulas B A, O'Hara M, Lochmuller H, et al. (1997) Use of the dog model for Duchenne muscular dystrophy in gene therapy trials. *Neuromuscul. Disord.* 7: 325-328.

13. Acland G M, Aguirre G D, Ray J, Zhang Q, Aleman T S, et al. (2001) Gene therapy restores vision in a canine model of childhood blindness. *Nat. Genet.* 28: 92-95.

14. Mount J D, Herzog R W, Tillson D M, Goodman S A, Robinson N, et al. (2002) Sustained phenotypic correction of hemophilia B dogs with a factor IX null mutation by liver-directed gene therapy. *Blood* 99: 2670-2676.

15. Ponder K P, Melniczek J R, Xu L, Weil M A, O'Malley T M, et al. (2002) Therapeutic neonatal hepatic gene therapy in mucopolysaccharidosis VII dogs. *Proc. Natl Acad. Sci. USA* 99: 13102-13107.

16. Bainbridge J W, Smith A J, Barker S S, Robbie S, Henderson R, et al. (2008) Effect of gene therapy on visual function in Leber's congenital amaurosis. *N. Engl. J. Med.* 358: 2231-2239.

17. Downs L M, Wallin-Hakansson B, Boursnell M, Marklund S, Hedhammar A, et al. (2011) A frameshift mutation in golden retriever dogs with progressive retinal atrophy endorses SLC4A3 as a candidate gene for human retinal degenerations. *PLoS ONE* 6: e21452.

18. Zangerl B, Goldstein O, Philp A R, Lindauer S J, Pearce-Kelling S E, et al. (2006) Identical mutation in a novel retinal gene causes progressive rod-cone degeneration in dogs and retinitis pigmentosa in humans. *Genomics* 88: 551-563.

19. OptiGen® (2008) PRA in Golden Retrievers. [online] Available at www.optiden.com/opt9_pra_goldenrtvr.html [accessed 24 Jun. 2010].

20. Nachury M V, Loktev A V, Zhang Q, Westlake C J, Peranen J, et al. (2007) A core complex of BBS proteins cooperates with the GTPase Rab8 to promote ciliary membrane biogenesis. *Cell* 129: 1201-1213.

21. Gasteiger E, Gattiker A, Hoogland C, Ivanyi I, Appel R D, et al. (2003) ExPASy: The proteomics server for in-depth protein knowledge and analysis. *Nucleic Acids Res.* 31: 3784-3788.

22. Riazuddin S A, Iqbal M, Wang Y, Masuda T, Chen Y, et al. (2010) A splice-site mutation in a retina-specific exon of BBS8 causes nonsyndromic retinitis pigmentosa. *Am. J. Hum. Genet.* 86: 805-812.

23. Ansley S J, Badano J L, Blacque O E, Hill J, Hoskins B E, et al. (2003) Basal body dysfunction is a likely cause of pleiotropic Bardet-Biedl syndrome. *Nature* 425: 628-633.

24. Stoetzel C, Laurier V, Faivre L, Megarbane A, Perrin-Schmitt F, et al. (2006) BBS8 is rarely mutated in a cohort of 128 Bardet-Biedl syndrome families. *J. Hum. Genet.* 51: 81-84.

25. Katsanis N, Ansley S J, Badano J L, Eichers E R, Lewis R A, et al. (2001) Triallelic inheritance in Bardet-Biedl syndrome, a Mendelian recessive disorder. *Science* 293: 2256-2259.

26. Rozen S, Skaletsky H (2000) Primer3 on the WWW for general users and for biologist programmers. *Methods Mol. Biol.* 132: 365-386.

27. Purcell S, Neale B, Todd-Brown K, Thomas L, Ferreira M A, et al. (2007) PLINK: a tool set for whole-genome association and population-based linkage analyses. *Am. J. Hum. Genet.* 81: 559-575.

28. Stephens M, Donnelly P (2003) A comparison of bayesian methods for haplotype reconstruction from population genotype data. *Am. J. Hum. Genet.* 73: 1162-1169.

29. Thompson J D, Higgins D G, Gibson T J (1994) CLUSTAL W: improving the sensitivity of progressive multiple sequence alignment through sequence weighting, position-specific gap penalties and weight matrix choice. *Nucleic Acids Res.* 22: 4673-4680.

30. Bonfield J K, Smith K, Staden R (1995) A new DNA sequence assembly program. *Nucleic Acids Res.* 23: 4992-4999.

---

The invention claimed is:

1. A method comprising:

assessing a canine mammal for the presence or absence of a single base deletion in TTC8 gene at position 63,129154 on chromosome 8 (CanFam 2.0) by obtaining a sample comprising a nucleic acid from the canine mammal and detecting the presence or absence of the single base deletion by amplifying a part of the TTC8 gene using a forward primer comprising SEQ ID NO:1 and a reverse primer comprising SEQ ID NO:2, wherein the canine mammal is a Golden Retriever.

2. The method according to claim 1, wherein the nucleic acid is genomic DNA.

3. The method according to claim 1, which further comprises the step of establishing whether or not the canine mammal is heterozygous or homozygous for the single base pair deletion within the TTC8 gene.

4. The method according to claim 3, wherein if the canine mammal is heterozygous for the genetic variation within the TTC8 gene, it is selected as being suitable for breeding with a canine mammal of the same breed which is homozygous for the wild-type TTC8 gene.

5. The method according to claim 3, wherein if the canine mammal is homozygous for the wild-type TTC8 gene, it is selected as being suitable for breeding with a canine mammal of the same breed which is homozygous or heterozygous for the wild-type TTC8 gene.

6. The method according to claim 1, wherein the sample is assessed for one or more other markers which are linked or associated with canine disorders.

7. has been amended to: The method according to claim 1, wherein the detecting further comprises determining the binding of oligonucleotide probes to the nucleic acid, wherein the probes comprise all or part of the wild-tpe or mutant TTC8 gene.

* * * * *

SEQUENCE LISTING

<160> NUMBER OF SEQ ID NOS: 9

<210> SEQ ID NO 1
<211> LENGTH: 19
<212> TYPE: DNA
<213> ORGANISM: Artificial
<220> FEATURE:
<223> OTHER INFORMATION: Synthetic Primer

<400> SEQUENCE: 1
tgccctttcc acagagcac                                              19

<210> SEQ ID NO 2
<211> LENGTH: 21
<212> TYPE: DNA
<213> ORGANISM: Artificial
<220> FEATURE:
<223> OTHER INFORMATION: Synthetic Primer

<400> SEQUENCE: 2
ccatgtctaa gcccttcaca a                                           21

-continued

```
<210> SEQ ID NO 3
<211> LENGTH: 19
<212> TYPE: DNA
<213> ORGANISM: Artificial
<220> FEATURE:
<223> OTHER INFORMATION: Synthetic Primer

<400> SEQUENCE: 3
ggcctttctc ctgcagact                                                  19

<210> SEQ ID NO 4
<211> LENGTH: 19
<212> TYPE: DNA
<213> ORGANISM: Artificial
<220> FEATURE:
<223> OTHER INFORMATION: Synthetic Primer

<400> SEQUENCE: 4
cagcttctca cggttggac                                                  19

<210> SEQ ID NO 5
<211> LENGTH: 20
<212> TYPE: DNA
<213> ORGANISM: Artificial
<220> FEATURE:
<223> OTHER INFORMATION: Synthetic Primer

<400> SEQUENCE: 5
agccatgtgc accaccctct                                                 20

<210> SEQ ID NO 6
<211> LENGTH: 22
<212> TYPE: DNA
<213> ORGANISM: Artificial
<220> FEATURE:
<223> OTHER INFORMATION: Synthetic Primer

<400> SEQUENCE: 6
tgagccatgt acaccaccct ct                                              22

<210> SEQ ID NO 7
<211> LENGTH: 21
<212> TYPE: DNA
<213> ORGANISM: Artificial
<220> FEATURE:
<223> OTHER INFORMATION: Synthetic Primer

<400> SEQUENCE: 7
agagcaacct tgtaacccgt a                                               21

<210> SEQ ID NO 8
<211> LENGTH: 21
<212> TYPE: DNA
<213> ORGANISM: Artificial
<220> FEATURE:
<223> OTHER INFORMATION: Synthetic Primer

<400> SEQUENCE: 8
ggaagaaggc aatgagaaag g                                               21

<210> SEQ ID NO 9
<211> LENGTH: 27
```

```
<212> TYPE: DNA
<213> ORGANISM: Canis lupus familiaris

<400> SEQUENCE: 9
cactctcagt acaaggactg gtggtgg                                              27
```